(12) United States Patent
Glick et al.

(10) Patent No.: US 6,248,111 B1
(45) Date of Patent: Jun. 19, 2001

(54) IOL INSERTION APPARATUS AND METHODS FOR USING SAME

(75) Inventors: Robert E. Glick, Lake Forest; Harish Makker, Mission Viejo; Robert D. Ott, Irvine, all of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/370,070

(22) Filed: Aug. 6, 1999

(51) Int. Cl.$^7$ ................................................. A61F 9/00
(52) U.S. Cl. ............................................................ 606/107
(58) Field of Search ............................................. 606/107

(56) References Cited

U.S. PATENT DOCUMENTS

| | | |
|---|---|---|
| 4,261,806 | 4/1981 | Asia et al. . |
| 4,681,102 | 7/1987 | Bartell . |
| 4,722,906 | 2/1988 | Guire . |
| 4,740,282 | 4/1988 | Gesser et al. . |
| 4,806,382 | 2/1989 | Goldberg et al. . |
| 4,842,889 | 6/1989 | Hu et al. . |
| 4,844,986 | 7/1989 | Karakelle et al. . |
| 4,919,130 | 4/1990 | Stoy et al. . |
| 4,973,493 | 11/1990 | Guire . |
| 4,979,959 | 12/1990 | Guire . |
| 5,028,597 | 7/1991 | Kodama et al. . |
| 5,073,166 | 12/1991 | Parks et al. . |
| 5,084,315 | 1/1992 | Karimi et al. . |
| 5,094,876 | 3/1992 | Goldberg et al. . |
| 5,098,618 | 3/1992 | Zelez . |
| 5,108,776 | 4/1992 | Goldberg et al. . |
| 5,130,160 | 7/1992 | Goldberg et al. . |
| 5,135,516 | 8/1992 | Sahatjian et al. . |
| 5,190,552 | 3/1993 | Kelman . |
| 5,217,492 | 6/1993 | Guire et al. . |
| 5,258,041 | 11/1993 | Guire et al. . |
| 5,263,992 | 11/1993 | Guire . |
| 5,290,548 | 3/1994 | Goldberg et al. . |
| 5,303,714 | 4/1994 | Abele et al. . |
| 5,304,182 | 4/1994 | Rheinish et al. . |
| 5,331,019 | 7/1994 | Payne, Jr. et al. . |
| 5,331,027 | 7/1994 | Whitbourne . |
| 5,336,263 | 8/1994 | Ersek et al. . |
| 5,425,734 | * 6/1995 | Blake ................................ 606/107 |
| 5,429,839 | 7/1995 | Graiver et al. . |
| 5,441,488 | 8/1995 | Shimura et al. . |
| 5,468,246 | * 11/1995 | Blake ................................ 606/107 |
| 5,474,562 | 12/1995 | Orchowski et al. . |
| 5,503,631 | 4/1996 | Onishi et al. . |
| 5,620,450 | 4/1997 | Eagles et al. . |
| 5,693,034 | 12/1997 | Buscemi et al. . |
| 5,772,667 | * 6/1998 | Blake ................................ 606/107 |
| 5,803,925 | 9/1998 | Yang et al. . |
| 5,876,406 | 3/1999 | Wolf et al. . |
| 5,947,976 | 9/1999 | Van Noy et al. . |

FOREIGN PATENT DOCUMENTS

| | | |
|---|---|---|
| 3610925 | 1/1987 | (DE) . |
| 0480809 | 4/1992 | (EP) . |
| 7900327 | 6/1979 | (WO) . |
| 9316176 | 8/1993 | (WO) . |
| 9420027 | 9/1994 | (WO) . |
| 9522287 | 8/1995 | (WO) . |
| 9622062 | 7/1996 | (WO) . |

* cited by examiner

*Primary Examiner*—Paul J. Hirsch
(74) *Attorney, Agent, or Firm*—Stout, Uxa, Bryan & Mullins; Frank J. Uxa

(57) ABSTRACT

Apparatus for inserting intraocular lenses (IOLs) into eyes include a hollow tube including a material and having an interior wall defining a hollow space through which an IOL is passed and an outlet through which the IOL is passed from the hollow space into an eye. The interior wall is configured, for example, roughened, so that a portion of the interior wall remains out of contact with the deformable optic of the IOL as the IOL passes through the hollow space. Advantageously reduced amounts of force are required to pass the IOL through the hollow space.

23 Claims, 2 Drawing Sheets

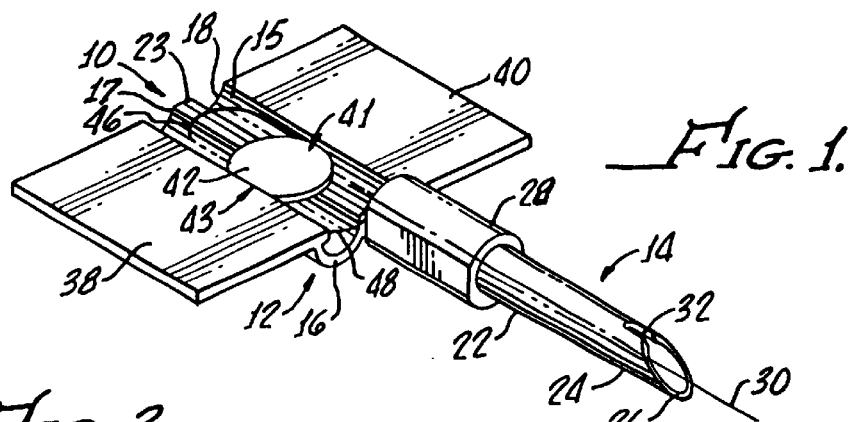
FIG. 1.
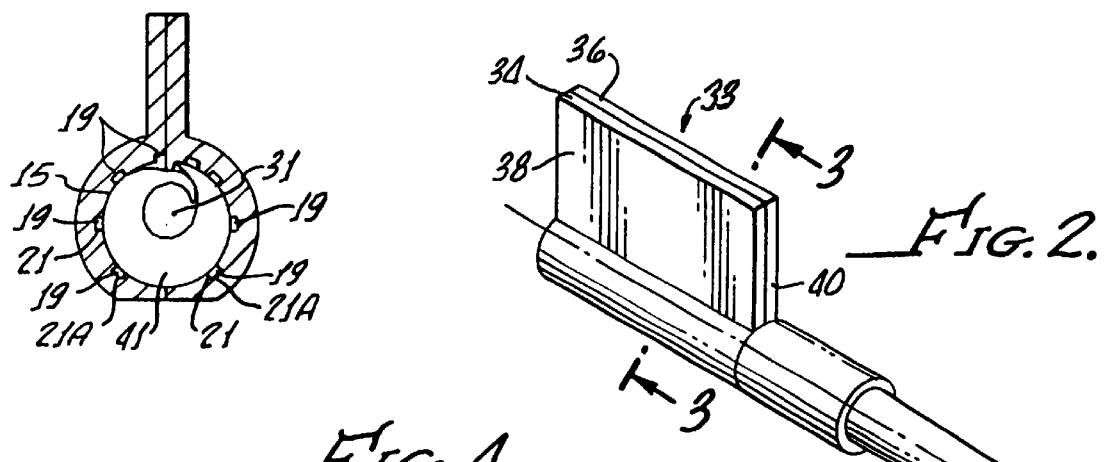
FIG. 3.
FIG. 2.
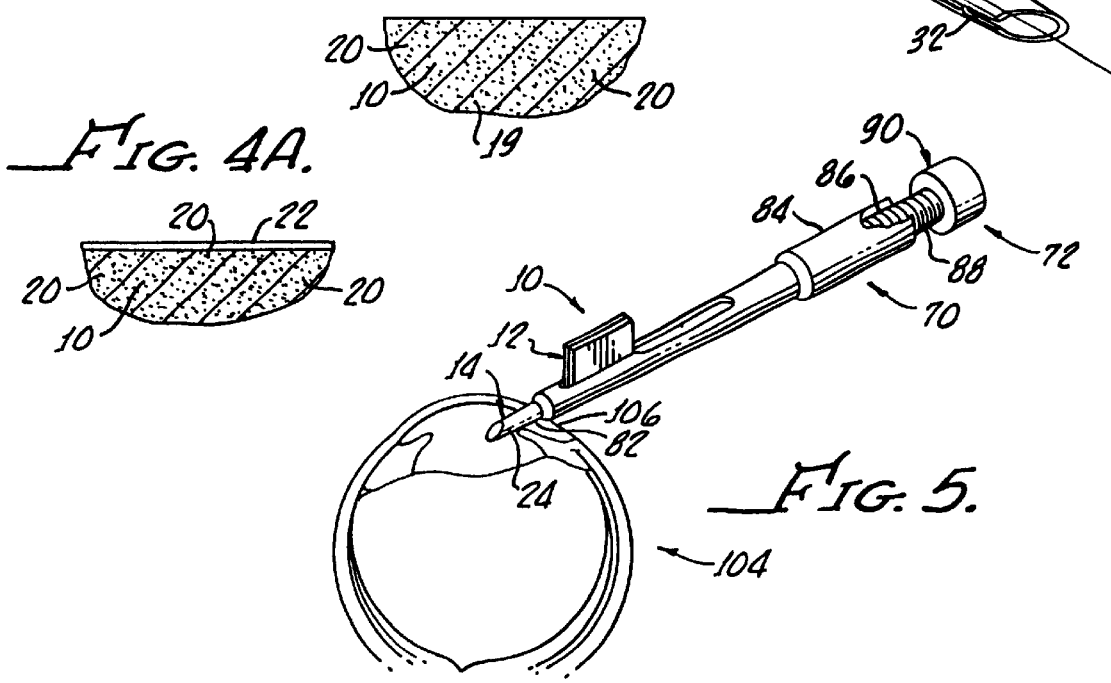
FIG. 4.
FIG. 4A.
FIG. 5.

IOL INSERTION APPARATUS AND METHODS FOR USING SAME

BACKGROUND OF THE INVENTION

The present invention relates to apparatus for inserting an intraocular lens through a small incision into an eye, and to methods for inserting an intraocular lens into an eye. More particularly, the invention relates to apparatus which are designed to facilitate inserting a foldable or deformable intraocular lens into an eye and to methods using such apparatus to insert such an intraocular lens into an eye.

An intraocular lens (IOL) is implanted in the eye, for example, as a replacement for the natural crystalline lens after cataract surgery or to alter the optical properties of (provide vision correction to) an eye in which the natural lens remains. IOLs often include an optic, and preferably at least one flexible fixation member or haptic which extends from the optic and becomes affixed in the eye to secure the lens in position. The optic normally includes an optically clear lens. Implantation of such IOLs into the eye involves making an incision in the eye. It is advantageous, to reduce trauma and speed healing, to have an incision size as small as possible.

IOLs are known which are foldable (deformable) so that the IOL can be inserted through a smaller incision into the eye. A substantial number of instruments have been proposed to aid in inserting such a foldable lens in the eye.

One additional factor to be considered in inserting foldable or deformable IOLs into the eye relates to the amount of force required for such inserting. Advantageously, the amount of force required is reduced, for example, to reduce the risk of damaging the IOL and to reduce the risk of detrimentally affecting the patient.

Makker et al U.S. Pat. No. 5,716,364 discloses a very useful apparatus for inserting IOLs including a lubricity enhancing component to facilitate the IOL insertion process and, preferably, to reduce the amount of force required. The disclosure of this patent is hereby incorporated in its entirety herein by reference.

There continues to be a need to provide IOL insertion apparatus which are effective to facilitate the passage of folded or deformed IOLs through the apparatus in a controlled manner without using excessive force.

SUMMARY OF THE INVENTION

New apparatus for injecting or inserting IOLs and methods for using such apparatus have been discovered. The present apparatus achieve reduced friction between the IOL and the insertion apparatus as the IOL is being passed through the insertion apparatus and into the eye. Thus, IOLs can be inserted using the present apparatus preferably with reduced amounts of force, for example, relative to prior art apparatus. The present apparatus are easy to produce and are straightforward in construction. The methods of use included in the present invention are straightforward and easy to practice, and may involve surgical techniques which are well practiced and conventionally used to insert IOLs into eyes.

In one broad aspect of the present invention, apparatus for inserting an IOL including a deformable optic through a small incision into an eye are provided. The apparatus comprises a hollow tube including a material, preferably a polymeric material. The hollow tube has an interior wall defining a hollow space through which the IOL is passed and an outlet through which the IOL is passed from the hollow space into the eye. In one embodiment, the interior wall is configured so that a portion of the interior wall remains out of contact with the deformable optic as the IOL passes through the hollow space. This reduced contact between the IOL and the interior wall of the hollow tube advantageously reduces the friction between the IOL and the hollow tube which, preferably, reduces the amount of force required to pass the IOL from a fixed position through the hollow space relative to the force required to pass an identical IOL including an identical deformable optic from a fixed position through a similar hollow space defined by a similar interior wall configured so that substantially all of the similar interior wall contacts the identical deformable optic as the identical IOL passes through the similar hollow space. The present apparatus preferably require reduced amounts of force to pass IOLs including deformable optics through the hollow space and into the eye relative to prior art apparatus.

The interior wall of the hollow tube may have any suitable configuration so that a portion of the interior wall remains out of contact with the deformable optic as the IOL passes through the hollow space. For example, at least a portion of the interior wall or surface can be roughened or include rifling. The interior surface can include at least one groove, preferably a plurality of spaced apart grooves, for example, such groove or grooves extending substantially parallel to the longitudinal axis of the hollow tube, that is one or more substantially longitudinal grooves. In a further embodiment, the interior wall includes a plurality of spaced apart inwardly extending projections or bumps which provide the desired configuration to the interior wall, as described herein.

In a very useful embodiment, the present apparatus further include a lubricity enhancing component secured, preferably physically secured, to the hollow tube and concentrated at or near the interior wall. This lubricity enhancing component is effective to facilitate the passage of the IOL through the hollow space. More preferably, the lubricity enhancing component is effective to further reduce the force needed to pass the IOL through the hollow space relative to the force needed to pass an identical IOL through the hollow space of a similar apparatus without the lubricity enhancing component.

By "physically" securing or bonding is meant, a non-covalent chemical bonding joining or coupling, and preferably a non-chemical bonding, joining or coupling. Some interaction, for example, some interaction, for example, ionic and/or electrical interactions may occur between the lubricity enhancing component and the other material or materials making up the hollow tube. However, the present "physical" securing or bonding is clearly distinguished from forming covalent chemical bonds between the lubricity enhancing component and the other material or materials making up the hollow tube.

As used herein, the term "concentrated" means that the lubricity enhancing component is located in a higher concentration at or near one or more portions, for example, the surfaces, of an article than at one or more other portions, for example, the interior, of the article. This includes the situation in which the lubricity enhancing component is located as a coating on the interior surface of the hollow tube and is not present in the hollow tube itself. Also included is a situation in which the hollow tube includes a concentration of lubricity enhancing component throughout with a locally higher concentration present at or near the interior surface of the hollow tube.

The interior wall may be exposed to a plasma. Alternately, the interior wall is not subjected to plasma exposure. In one embodiment, the interior wall is a plasma-exposed interior wall which has an enhanced ability to physically secure the lubricity enhancing component relative to a substantially identical interior wall which is not plasma exposed. The plasma-exposed interior wall preferably facilitates forming the lubricity enhancing component concentrated at or near the interior wall.

A suitable lubricity component which functions as described herein may be employed. The lubricity enhancing component may be selected from hydrophilic components, oleophilic components and mixtures thereof. In a very useful embodiment, the lubricity enhancing component is selected from water soluble components and mixtures thereof. Such water soluble components have the substantial advantage of dispersing relatively rapidly in the eye, for example, after being introduced into the eye with the IOL. Thus, the use of water soluble lubricity enhancing components reduce the risk of long term, or even transient, detrimental effects on the eye or on the patient or on the patient's vision caused by the presence of the lubricity enhancing component.

The present apparatus includes a hollow tube which preferably is sized to pass the IOL into the eye through an incision no larger than about 3.5 mm. The hollow tube may include a surface coating of a covalently bonded lubricity enhancing component in an amount effective to further facilitate the passage of the IOL through the hollow space.

Methods for inserting an IOL including a deformable optic into an eye are included within the scope of the present invention. These methods comprise placing the outlet of a hollow tube of the present apparatus in or in proximity to an incision in an eye. The IOL is passed from the hollow space through the outlet into the eye. In one very useful embodiment, the present methods further comprise providing a liquid composition, preferably an aqueous balanced salt solution (BSS), a liquid visco elastic composition and mixtures thereof, in the hollow space with the IOL. This liquid composition is effective to facilitate the passing step.

Overall, the present methods preferably provide for reduced and controlled amounts of force effective to pass a folded or otherwise deformed IOL from the present apparatus into the eye where the lens can be properly positioned for safe and effective use.

The "reduced force" feature of the present invention is useful, and can result in reducing the size of the incision through which the IOL is inserted. However, this "reduced force" feature is useful even when no reduction in the size of the incision is obtained. The use of reduced force allows the surgeon to have more control of the rate at which the IOL is inserted into the eye and, in addition, reduces the risk of damage to the eye during IOL insertion. The IOL may be allowed to dwell or remain stationary or in a fixed position in the hollow tube for a period of time, for example, on the order of about 30 seconds to about 10 minutes or more, while the surgeon prepares to insert the IOL. Previously, such dwelling or remaining in a fixed position in the hollow tube has increased the risk of damage to the IOL when the IOL is finally moved. The present apparatus with an interior wall configured as described herein reduces the risk of IOL damage even after the IOL is maintained in a fixed position in the hollow tube.

The material from which the hollow tube is preferably made is a polymeric material, for example, a hydrophobic polymeric material, more preferably selected from polyolefins, such as polypropylene and the like materials.

Any and all features described herein and combinations of such features are included within the scope of the present invention provided that the features of any such combination are not mutually inconsistent.

These and other aspects and advantages of the present invention will become apparent in the following detailed description and claims, particularly when considered in conjunction with the accompanying drawings in which like parts bear like reference numerals.

BRIEF DESCRIPTION OF THE DRAWINGS

FIG. 1 is a front side view, in perspective, of an apparatus in accordance with the present invention with the load chamber in the open position.

FIG. 2 is a side view, in perspective, of the apparatus shown in FIG. 1 with the load chamber in the closed position.

FIG. 3 is a cross-sectional view taken generally along line 3—3 of FIG. 2.

FIG. 4 is a fragmentary, schematic illustration of a small portion of the apparatus shown in FIG. 1.

FIG. 4A is a fragmentary, schematic illustration of a small portion of a modified embodiment of the apparatus shown in FIG. 1 which includes a coating.

FIG. 5 is a somewhat schematic illustration showing the apparatus shown in FIG. 1, in combination with a hand piece partially exploded, being used to insert an IOL into an eye.

DETAILED DESCRIPTION OF THE DRAWINGS

Figure 6:
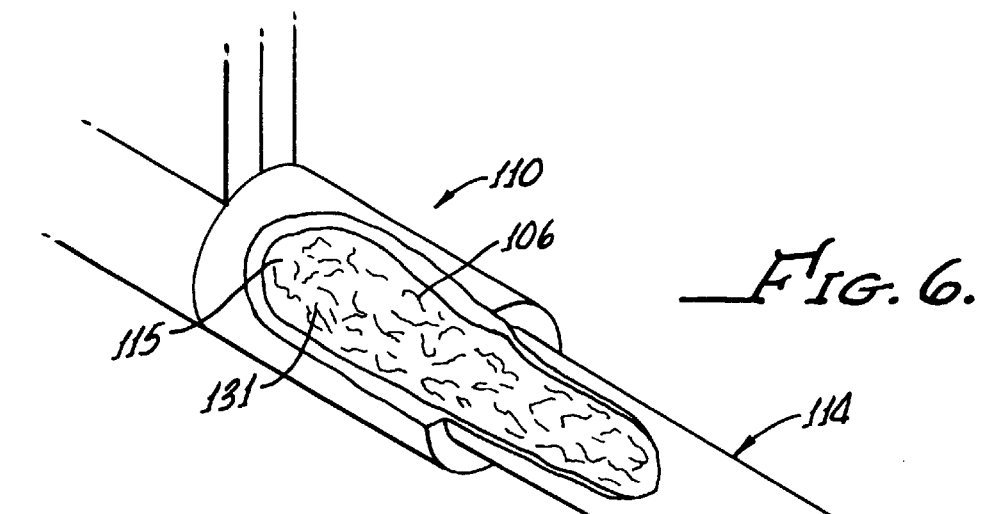
FIG. 6 is a partial cut away view, in perspective of a further embodiment of an apparatus in accordance with the present invention.

FIG. 1 illustrates an IOL inserter, shown generally at 10, including a load chamber 12 and an injection tube 14. The IOL inserter 10 is made of polypropylene to which has been physically added an amount, for example, in the range of about 0.1% to about 5% by weight of the inserter, of a water soluble lubricity enhancing component, such as hydroxypropylmethyl cellulose (HPMC).

The lubricity enhancing component is physically admixed with the other material from which the inserter 10 is made, preferably prior to forming, for example, molding, the inserter. In a particularly useful embodiment, the lubricity enhancing component is combined with the other material, for example, a polymeric material, such as polypropylene, while the material is in the molten or fluid state. The lubricity enhancing component can be blended in this material so that it is substantially uniformly distributed throughout the material. The material is then placed in a mold or similar device suitable for forming the inserter 10. After the inserter 10 is formed, the lubricity enhancing component remains substantially uniformly distributed throughout the inserter.

In addition, the inserter 10 includes an interior surface 15 which extends from the proximal end 17 to the distal opening 26. As shown best in FIG. 3, interior surface 15 is formed with a plurality of longitudinally extending grooves 19 which extend a substantial distance within the inserter 10, for example, from the proximal end 17 to a position in the injector tube proximal of the distal opening 26. The grooves 15 can, if desired, extend from the proximal end 17 to the distal opening 26. However, it may be advantageous, because of space and size considerations, to have the interior surface 15 in the distal end portion 24 of injection tube 14 be substantially smooth, that is without grooves 19.

The longitudinal grooves 19, which can be considered recesses in the interior surface 15, reduce the contact area between the interior surface and the optic 41 of IOL 43. As best shown in FIG. 3, the deformable optic 41 is folded within the hollow space 31 of inserter 10 so that the optic does not come in contact with substantial portions of the sidewalls 21 and the closed end wall 21A of the longitudinal grooves 19.

Inserter 10 can be produced to include the longitudinal grooves 19 using conventional molding techniques which are well known in the art. In particular, the interior surface 15 preferably is formed, for example, during the molding inserter 10, with longitudinal grooves 19.

Once the inserter 10 is formed, it is processed to provide enhanced lubricity. The inserter 10 is exposed to an effective plasma. For example, the inserter 10 can be placed in a chamber containing a plasma. The plasma may have its origin for any of a variety of materials, preferably gases, in particular gases such as oxygen, helium, nitrogen, argon and mixtures thereof. More preferably an oxygen-containing plasma is used.

In accordance with one embodiment of the present invention, radio frequency, inductively-coupled plasma is produced in a plasma chamber by charging the chamber with gas, e.g., oxygen, preferably at a sub-atmospheric pressure such as about 0.01 torr (mm Hg) or greater, more preferably at a pressure in the range of about 0.01 torr to about 0.3 torr or about 0.5 torr or about 1.0 torr. The preferred output power is in the range of about 10 watts to about 600 watts.

The inserter 10 is preferably exposed to the plasma for a period of time in the range of about 15 seconds to about 240 minutes and more preferably about 30 seconds to about 200 minutes. However, the specific gas, exposure time, power and/or other parameters may be varied depending upon the equipment and the particular inserter and inserter components involved, and can be readily optimized based on the disclosure herein using routine experimentation.

In addition, inserter 10 is subjected to conditions effective to form interior walls on or near which is present a higher concentration of lubricity enhancing component relative to the lubricity enhancing component concentration present in the interior of the inserter. A particularly useful embodiment involves subjecting the inserter to an elevated temperature for a time effective to cause the lubricity enhancing component to migrate toward the surfaces, for example, the interior surface, of the inserter. A common name for this phenomenon is "blooming". Preferably, the inserter 10 is subjected to elevated temperatures of at least about 35° C., more preferably in the range of about 40° C. or about 45° C. to about 100° C. or about 120° C., for a time in the range of about 6 hours to about 150 hours and more preferably in the range of about 8 hours to about 120 hours.

Alternately, the inserter 10 can be formed and then treated with a lubricity enhancing component, preferably selected from oleophilic components, hydrophilic components and mixtures thereof, and more preferably water soluble components. For example, the inserter 10 can be immersed in or sprayed with a lubricity enhancing component or a medium, such as an aqueous medium, including a lubricity enhancing component one or more times so as to provide a surface coating, preferably a substantially uniform surface coating of the lubricity enhancing component, for example, on the interior surfaces or walls of the inserter. The inserter 10 is exposed to a plasma, as discussed elsewhere herein, either prior to or after, preferably prior to, providing a surface coating of lubricity enhancing component.

In any event, the lubricity enhancing component is present in an amount effective, in combination with the plasma exposing step, to enhance or facilitate the passage of the IOL through the inserter 10 into the eye. It should be noted that the lubricity enhancing component need not be substantially present within the inserter 10 as discrete particles. However, preferably substantially no covalent chemical bonds exist between the lubricity enhancing component and the other material making up the inserter 10.

The lubricity enhancing components useful in the present invention may be selected from suitable components which function as described herein. Although the lubricity enhancing component preferably is inhibited from passing into the eye during use of the present apparatus, lubricity enhancing components which are substantially non-irritating to ocular tissue and/or are substantially biocompatible with ocular tissue are particularly useful in accordance with the present invention. As discussed elsewhere herein, water soluble lubricity enhancing components are particularly useful.

The lubricity enhancing component is present in an amount effective to enhance the lubricity of the interior wall of the hollow tube defining a hollow space through which the IOL passes in being inserted into the eye. Such lubricity enhancing components are preferably effective to provide such enhanced lubricity for relatively long periods of time, for example, for at least about 1 month or at least about 3 months or at least about 6 months, so that the IOL inserter has a relatively long shelf life and can be used after being packaged and stored for such relatively long periods of time and still obtain the substantial enhanced lubricity benefits.

The physical securing or bonding of the lubricity enhancing component to the IOL inserter preferably is effective to reduce the amount of this component which is passed into the eye as the IOL is inserted into the eye. In other words, it is preferred that such physical securing or bonding is effective to inhibit the lubricity enhancing component from passing into the eye as the IOL is inserted into the eye. Thus, the present invention conveniently provides for enhanced lubricity and ease of inserting an IOL into an eye while, at the same time, reducing the amount of lubricity enhancing component in the eye and eliminating the need for any covalent chemical reaction or reactions between the material of the inserter and the lubricity enhancing component.

Particularly useful oleophilic components include, but are not limited to, those selected from carboxylic acids having about 10 to about 30, carbon atoms per molecule, glycerol esters of such carboxylic acids, such as glycerol monostearate, glycerol monopalmitate, glycerol monooleate and the like, and mixtures thereof.

Particularly useful hydrophilic lubricity enhancing components include, but are not limited to, those selected from polyethylene glycol, polyvinylpyrrolidone, poly (N-vinyl lactams), polyacrylic acid, polyethylene oxide, polyvinyl alcohol, polysaccharides, carboxy methyl cellulose, hydroxy alkyl celluloses, such as hydroxypropylmethyl cellulose and the like, polymethacrylic acid, polyacrylamide, polypeptides, poly sodium styrene sulfonate, polyhydroxyethyl methacrylate, heparin and the like and mixtures thereof. If a hydrophilic lubricity enhancing component is employed, it is preferred that the IOL inserter be immersed or otherwise contacted with water, for example, a saline solution, to hydrate the hydrophilic component. Such hydration is effective to facilitate the lubricity enhancing characteristics of the hydrophilic component.

In a very useful embodiment, the lubricity enhancing component is water soluble. That is, the present water soluble lubricity enhancing components are soluble in or form solutions with the aqueous medium of the eye into which the IOL is inserted. Water soluble compounds such are effective to substantially eliminate long term contamination of the IOL by the lubricity enhancing component contained in the cartridge. Various water soluble compounds, for example, as set forth herein, can be readily compounded into polymeric materials such as polypropylene that are used to produce the present inserters. The water soluble lubricity enhancing components may be selected from hydrophilic components, water soluble surfactant components and mixtures thereof. Further examples of water soluble lubricity enhancing components include, but are not limited to, polyethylene glycol, polyvinylpyrrolidone, polyvinyl alcohol, polysaccharides, carboxymethyl cellulose, hydroxyalkyl celluloses, polyacrylamide, polyhydroxyethyl methacrylate, water soluble surfactant components and the like and mixtures thereof.

Although the present lubricity enhancing components can be chosen from anionic surfactants, cationic surfactants and amphoteric surfactants, if a water soluble surfactant component is employed as the lubricity enhancing component in the present invention, a nonionic surfactant component is preferred.

In general, a surfactant component is a surface active material which is effective, when present in water, to reduce the surface tension of water. Often, surfactants include a hydrophilic portion and a hydrophobic portion.

Examples of useful water soluble surfactant components include, but are not limited to, nonionic surfactants such as those compounds or compositions produced by the reaction, for example, condensation, of a hydrophilic entity, for example containing alkylene oxide groups, with an organic hydrophobic moiety, for example, which may be aliphatic or alkyl aromatic in nature.

Preferred water soluble surfactants include, but are not limited to, those derived from the condensation of ethylene oxide with the product resulting from the reaction of propylene oxide and ethylene diamine varied in composition depending upon the balance between the hydrophobic and hydrophilic elements desired. For example, such surfactants include compounds containing about 40 % to about 80% by weight of polyoxyethylene, e.g., having a molecular weight in a range of about 5,000 to about 15,000, resulting from the reaction of ethylene oxide with the reaction product of ethylene diamine and excess propylene oxide, e.g., having a molecular weight in the range of about 2,000 to about 4,000. Also included are condensation products of aliphatic alcohols having about 8 or about 10 to about 14 or about 18 carbon atoms, in either straight chain or branched chain configuration, with ethylene oxide, such as a coconut alcohol/ethylene oxide condensate including about 10 to about 30 moles of ethylene oxide per mole of coconut alcohol.

Particularly preferred nonionic surfactants include, but are not limited to, block copolymers of ethylene oxide and propylene oxide, such as those having a molecular weight in the range of about 1,100 to about 150,000, ranging from flowable liquids of varying viscosities, to paste, prills and cast solids at room temperature, that is about 22° C. Examples of such nonionic surfactants are sold by BASF Corporation under the trademark Pluronic, such as Pluronic F-68, F-88, F-108, F-127 and the like and mixtures thereof.

Such water soluble lubricity enhancing components are advantageous, for example, since they are readily dissolved in the eye's aqueous medium and, consequently, are rapidly dissipated. The lubricity enhancing component may be chosen to have, in an aqueous solution, an index of refraction substantially similar to the optic of the IOL being inserted or the aqueous medium, that is the aqueous humor, in the eye into which the IOL is inserted. Lubricity enhancing components with such substantially similar indexes of refraction, if they are present in the eye, have a reduced, or even substantially no, risk of impairing the vision of the patient.

In one useful embodiment, mixtures of water soluble lubricity enhancing components, as described herein, and oleophilic lubricity enhancing components are employed. The water soluble lubricity enhancing component or components in such mixtures preferably are present in a major amount, that is at least about 50% by weight, of the total lubricity enhancing components present. Such mixtures provide substantial lubricity enhancing benefits while, at the same time, being more effectively dispersed in and/or removed from the eye relative to a comparably effective amount of oleophilic lubricity enhancing component without the water soluble lubricity enhancing component.

In addition to the physically secured or bonded lubricity enhancing component, the inserter 10 may also include a covalently bonded lubricity enhancing component, for example, as a coating on the exposed surfaces, such as the interior surfaces of the inserter. Such additional covalently bonded lubricity enhancing component is effective to further enhance the lubricity of inserter 10. The covalently bonded lubricity enhancing component can be included in or on the inserter 10 in any suitable manner.

FIGS. 1 to 4, 4A and 5 illustrate the use of IOL inserter 10 including a plurality of longitudinal grooves 19 and an effective amount of physically secured or bonded lubricity enhancing component 20 (FIG. 4) or 22 (FIG. 4A) concentrated at or near the interior surfaces thereof.

Load chamber 12 includes a first member 16 and a second member 18 which are secured or joined together and are hingeably moveable relative to each other along line 23, which is parallel to the longitudinal axis 30 of inserter 10.

Injection tube 14 includes a proximal end portion 22. A reinforcing collar 28 is substantially coincidental with the proximal end portion 22.

Open distal end 26 is beveled at an angle of about 45° relative to the longitudinal axis 30 of the inserter 10.

Injection tube 14 includes a through slot 32 which extends from the open distal end 26 distally and terminates prior to the proximal end portion 22 of injection tube 14. Through slot 32 is elongated in a direction parallel to the longitudinal axis 30 of inserter 10.

As shown in FIG. 1, inserter 10 is in the opened position. In contrast, in FIG. 2, inserter 10 is shown in the closed position. In the closed position, the load chamber 12 includes a top 33 which is a combination of top surfaces 34 and 36 of first wing 38 and second wing 40, respectively, of first member 16 and second member 18, respectively. First and second wings 38 and 40 are effective for a human user of inserter 10 to hold and manipulate the inserter 10 while using it, as described elsewhere herein.

Inserter 10 is described in more detail with reference to FIG. 5, which shows the inserter in combination with hand piece 70 and push rod member 72. When used in combination with hand piece 70, the load chamber 12 of inserter 10 is in the closed position, as shown in FIG. 5.

The proximal end portion 84 of hand piece 70 includes threads 86 which are adapted to engage and mate with threads 88 of the proximal segment 90 of push rod member 72. Push rod member 72 extends distally and is adapted to pass through hollow space 31 and out of open distal end 26. Hand piece 70 and push rod member 72 are made of metal, such as surgical grade stainless steel or the like metals.

Inserter 10 is operated and functions as follows. When it is desired to load an IOL into inserter 10, the inserter is placed, for example, manually placed, in a configuration as shown in FIG. 1. With load chamber 12 in the opened position, an IOL, such as is shown generally at 43, is placed, for example, using forceps, in between first and second members 16 and 18. This placement is such that the anterior face 42 of optic 41 faces upwardly, as shown in FIG. 1. The optic 41 may be made of a silicone polymeric material. The filament haptics 46 and 48 of IOL 43 are located as shown in FIG. 1, so that the fixation members are located generally parallel to, rather than transverse to, the longitudinal axis 30.

An effective amount of a liquid composition, such as an aqueous balanced salt solution (BSS) and/or a visco elastic material, for example, an aqueous solution of sodium hyaluronate, other conventional visco elastic components, and the like and mixtures thereof, is added to facilitate the passage of the IOL 43 through the hollow space 31 and into the eye.

With IOL 43 placed as shown in FIG. 1, first and second members 16 and 18 are hingeably moved relative to each other, for example, by manually bringing first and second wings 38 and 40 together, to place the load chamber 12 in the closed position, as shown in FIG. 2. With load chamber 12 in the closed position, IOL 43 is in a folded state, that is optic 41 is folded. The relative movement of first and second members 16 and 18 to move the load chamber from the open position to the closed position is effective to fold the lens. The folded IOL 43 is now located in the hollow space 31 defined by interior wall 15 with longitudinal grooves 19.

With the inserter 10 configured as shown in FIG. 2 the inserter 10 is placed in association with hand piece 70. In this configuration, shown generally in FIG. 5, the distal end portion 24 of injection tube 14 extends distally beyond the distal end 82 of hand piece 70.

With inserter 10 so placed relative to hand piece 70, push rod member 72 is placed into the hollow space 31 starting at the proximal end. As threads 88 come in contact with and engage threads 86, the push rod member 72 is rotated, so as to thread the push rod member onto the proximal end portion 84 of hand piece 70. By gradually moving push rod member 72 through hollow space 31, the folded IOL 43 is urged to move through the hollow space, through open distal end 26 and into the eye.

Referring now to FIG. 5, the IOL 43 is to be placed in eye 104 into an area formerly occupied by the natural lens of the eye. FIG. 5 shows the sclera 106 having an incision through which the distal end portion 24 of injection tube 14 is passed. Alternately, the incision can be made through the cornea. Distal end portion 24 has a sufficiently small cross-section to pass into the eye 104 through a 3.0 mm incision in the sclera 122.

The injection tube 14 is manipulated within eye 104 until it is positioned so that IOL 43 can be properly positioned in eye 104, that is in the anterior chamber, the posterior chamber, the capsular bag or in the sulcus, after being released. Thus, the surgeon is able to controllably position the distal end portion 24 of injection tube 14, with IOL 43 in the proximal portion of the hollow space 31. Once distal end portion 24 is so positioned, the rod member 72 is urged distally to pass the IOL 43 through the hollow space 31, through the open distal end 26 of injection tube 14 and into the eye 104.

A reduced amount of force is required to push IOL 43 through the hollow space 31 and into the eye 104 even after the IOL is maintained in a fixed position in inserter 10 for a period of time to allow the surgeon to properly position the injector tube 14 in the eye. This reduced amount of force is relative to the force required to push an identical IOL through a similar hollow space defined by a substantially smooth interior wall, that is an interior wall substantially all of which is contacted by the IOL optic as the IOL passes through the hollow space.

After the IOL 100 has been inserted into the eye, the push rod member 72 is moved proximally into the injection tube 14 and the distal end portion 24 of the injection tube is removed from the eye. If needed, the IOL 100 can be re-positioned in the eye by a small, bent needle or similar tool inserted into the same incision.

Once the IOL 100 is properly positioned in eye 120 and inserter 10 is withdrawn from the eye, the incision in the sclera may be mended, for example, using conventional techniques. After use, inserter 10 is preferably disposed of. Hand piece 70 and push rod member 72 can be reused, after sterilization/disinfection.

FIG. 6 illustrates a further embodiment of an IOL inserter, shown generally at 110, in accordance with the present invention. Except as expressly described herein, inserter 110 is structured and functions similarly to inserter 10. Components of inserter 110 which correspond to components of inserter 10 are identified by the same reference numeral increased by 100.

The primary difference between inserter 110 and inserter 10 relates to the configuration of interior wall 115. Specifically, interior wall 115 does not include the longitudinal grooves present in the interior wall 15 of inserter 10. Interior wall 115 includes roughening, shown generally at 106. This roughening, which may be considered random roughening, is produced at the time of formation of the inserter 110. For example, the roughened surface finish can be achieved by producing roughened core pins with finishes of SPI B-2 or greater as defined by the Society of the Plastics Industry (SPI) mold finish guide. The roughened core pins are used to injection mold the inserter 110. Other methods may be employed to obtain the desired degree of roughening of interior wall 115. This roughening extends from the proximal end of the inserter 110 to a point which is proximal at the distal end opening 126 of injection tube 114.

Roughening 106 is such that a portion of the interior wall 115 of inserter 110 remains out of contact with a deformable optic of an IOL which is passed through the hollow space 131 defined by the interior wall 115 insertion into the eye. In use, inserter 110 performs substantially similarly to inserter 10. Inserter 110 advantageously requires a reduced amount of force to pass an IOL through the hollow space into the eye relative to an inserter having a substantially smooth interior wall.

Figure 7:
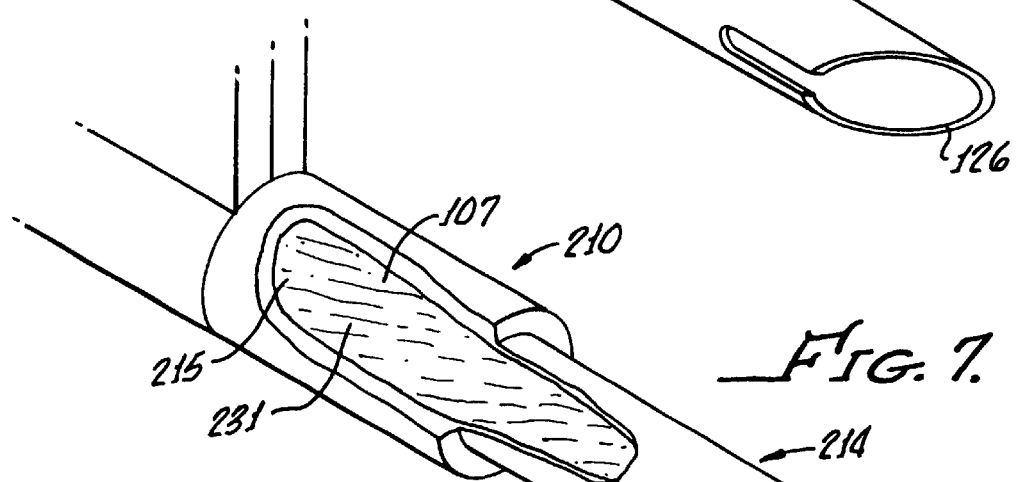
FIG. 7 is a partial cut away view, in perspective of an additional embodiment of an apparatus in accordance with the present invention.

FIG. 7 illustrates an additional embodiment of an IOL inserter, shown generally at 210, in accordance with the present invention. Except as expressly described herein, inserter 210 is structured and functions similarly to inserter 10. Components of inserter 210 which correspond to components of inserter 10 are identified by the same reference numeral increased by 200.

The primary difference between inserter 210 and inserter 10 relates to the configuration of interior wall 215. Specifically, interior wall 215 does not include the longitudinal grooves present in the interior wall 15 of inserter 10. Interior wall 215 does include rifling shown schematically at 107. This rifling, which may be considered a form of curved or even spiral grooves, is produced at the time of formation of the inserter 210, for example, using a suitably configured core pin in injector molding inserter 210, similarly to the method described previously with regard to the inserter 110. Other methods of providing the rifling can be employed. The rifling 107 extends from the proximal end of the inserter 210 to a point which is proximal at the distal end opening 226 of injection tube 214.

Rifling 107 is such that a portion of the interior wall 215 of inserter 210 remains out of contact with a deformable optic of an IOL which is passed through the hollow space 231 defined by the interior wall 215 for insertion into the eye. In use, inserter 210 performs substantially similarly to inserter 10. Inserter 210 advantageously requires a reduced amount of force to pass an IOL through the hollow space into the eye relative to an inserter having a substantially smooth interior wall.

Figure 8:
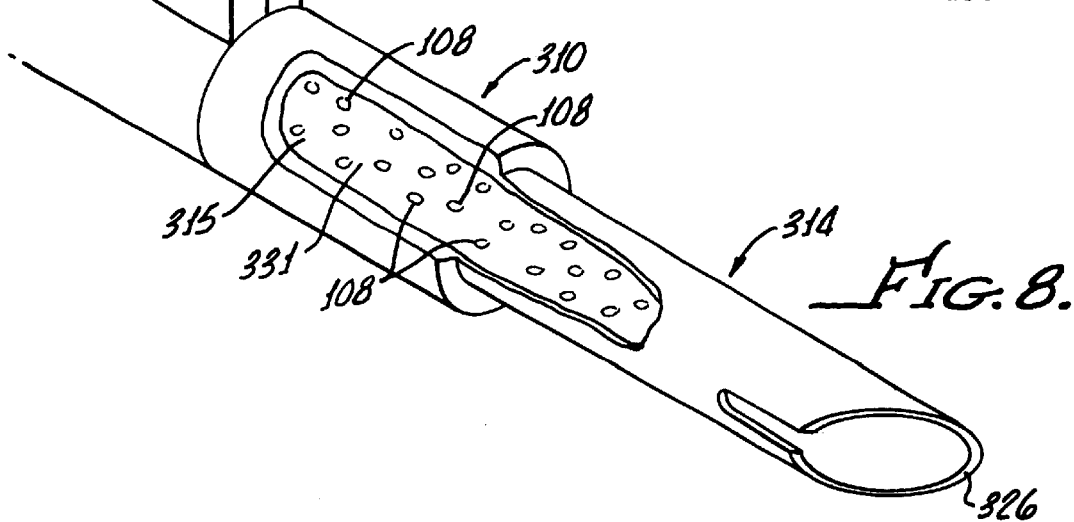
FIG. 8 is a partial cut away view, in perspective of another embodiment of an apparatus in accordance with the present invention.

FIG. 8 illustrates another embodiment of an IOL inserter, shown generally at 310, in accordance with the present invention. Except as expressly described herein, inserter 310 is structured and functions similarly to inserter 10. Components of inserter 310 which correspond to components of inserter 10 are identified by the same reference numeral increased by 300.

The primary difference between inserter 310 and inserter 10 relates to the configuration of interior wall 315. Specifically, interior wall 315 does not include the longitudinal grooves present in the interior wall 15 of inserter 10. Interior wall 315 includes a plurality of inwardly extending projections or bumps 108. These projections 108 are produced at the time of formation of the inserter 310, for example, using a suitably configured core pin in injection molding inserter 310. These projections 108 extend from the proximal end of the inserter 310 to a point which is proximal at the distal end opening 326 of injection tube 314.

Projections 108 are such that a portion of the interior wall 315 of inserter 310 remains out of contact with a deformable optic of an IOL which is passed through the hollow space 331 defined by the interior wall 315 for insertion into the eye. In use, inserter 310 performs substantially similarly to inserter 10. Inserter 310 advantageously requires a reduced amount of force to pass an IOL through the hollow space into the eye relative to an inserter having a substantially smooth interior wall.

While this invention has been described with respect of various specific examples and embodiments, it is to be understood that the invention is not limited thereto and that it can be variously practiced within the scope of the following claims.

What is claimed is:

1. An apparatus for inserting an intraocular lens including a deformed optic through a small incision into an eye comprising:
   a hollow tube including a material and having an interior wall defining a hollow space through which an intraocular lens including a deformed optic is passed and an outlet through which the intraocular lens is passed from the hollow space into an eye, the interior wall including a plurality of spaced apart longitudinal grooves, the interior wall being configured so that a portion of the interior wall remains out of contact with the deformed olptic as the intraocular lens passes through the hollow space and so as to reduce the amount of force required to pass the intraocular lens including a deformed optic from a fixed position in the hollow tube through the outlet into an eye relative to the amount of force required to pass an identical intraocular lens into an eye from a similar fixed position in a similar apparatus having a substantially smooth interior wall.

2. The apparatus of claim 1 wherein the at least a portion of the interior wall includes rifling.

3. The apparatus of claim 1 wherein said material is a polymeric material.

4. The apparatus of claim 1 which further comprises a lubricity enhancing component secured to the hollow tube and concentrated at or near the interior wall and being effective to facilitate the passage of the intraocular lens through the hollow space.

5. The apparatus of claim 4 wherein the lubricity enhancing component is effective to reduce the force needed to pass the intraocular lens through the hollow space relative to the force needed to pass an identical intraocular lens through the hollow space of a similar apparatus without the lubricity enhancing component.

6. The apparatus of claim 4 wherein the lubricity enhancing component is physically secured to the hollow tube.

7. The apparatus of claim 6 wherein the interior wall is a plasma-exposed interior wall which has an enhanced ability to physically secure the lubricity enhancing component relative to a substantially identical interior wall which is not plasma exposed.

8. A method for inserting an intraocular lens including a deformable optic into an eye comprising:
   placing the outlet of the apparatus of claim 1 in or in proximity to an incision in an eye; and
   passing an intraocular lens from the hollow space through the outlet of the apparatus into the eye.

9. The method of claim 8 wherein the apparatus further comprises a lubricity enhancing component secured to the hollow tube and concentrated at or near the interior wall and being effective to facilitate the passage of the intraocular lens through the hollow space, and which further comprises providing a liquid composition in the hollow space with the intraocular lens, the liquid composition being effective to facilitate the passing step.

10. The apparatus of claim 1 wherein at least a portion of the interior wall is roughened.

11. An apparatus for inserting an intraocular lens including a deformable optic through a small incision into an eye comprising:
   a hollow tube including a material and having an interior wall defining a hollow space through which an intraocular lens including a deformable optic is passed and an outlet through which the intraocular lens is passed from the hollow space into an eye; and
   the interior wall includes a plurality of spaced apart inwardly extending projections, each of the projections being surrounded by a substantially smooth surface, the interior wall being configured so to reduce the amount of force required to pass the intraocular lens from a fixed position in the hollow space through the outlet into an eye relative to the amount of force required to pass an identical intraocular lens into an eye from a similar fixed position in a similar apparatus having a substantially smooth interior wall.

12. The apparatus of claim 11 wherein the interior wall has a configuration so that a reduced amount of force is required to pass the intraocular lens from a fixed position in the hollow tube through the outlet into an eye relative to the amount of force required to pass an identical intraocular lens into an eye from similar fixed position in a similar apparatus having a similar interior wall configured so that substantially all of the similar interior surface directly contacts the deformable optic as the identical intraocular lens passes through the similar hollow space.

13. The apparatus of claim 11 wherein at least a portion of the interior wall is roughened.

14. The apparatus of claim 11 wherein at least a portion of the interior wall includes rifling.

15. The apparatus of claim 11 wherein said material is a polymeric material.

16. The apparatus of claim 11 which further comprises a lubricity enhancing component secured to the hollow tube and concentrated at or near the interior wall and being effective to facilitate the passage of the intraocular lens through the hollow space.

17. The apparatus of claim 16 wherein the lubricity enhancing component is effective to reduce the force needed to pass the intraocular lens through the hollow space relative to the force needed to pass an identical intraocular lens through the hollow space of a similar apparatus without the lubricity enhancing component.

18. The apparatus of claim 16 wherein the lubricity enhancing component is physically secured to the hollow tube.

19. The apparatus of claim 18 wherein the interior wall is a plasma-exposed interior wall which has an enhanced ability to physically secure the lubricity enhancing component relative to a substantially identical interior wall which is not plasma exposed.

20. The apparatus of claim 11 wherein the interior wall is configured so that a portion of the interior wall remains out of contact with the deformable optic as the intraocular lens passes through the hollow space.

21. A method for inserting an intraocular lens including a deformable optic into an eye comprising:

placing the outlet of the apparatus of claim 11 in or in proximity to an incision in an eye; and passing an intraocular lens from the hollow space through the outlet of the apparatus into the eye.

22. The method of claim 21 wherein the apparatus further comprises a lubricity enhancing component secured to the hollow tube and concentrated at or near the interior wall and being effective to facilitate the passage of the intraocular lens through the hollow space.

23. The method of claim 22 which further comprises providing a liquid composition in the hollow space with the intraocular lens, the liquid composition being effective to facilitate the passing step.

* * * * *